United States Patent [19]

Boersma et al.

[11] 4,337,176
[45] Jun. 29, 1982

[54] PROCESS FOR THE PREPARATION OF CRYSTALLINE SILICATES

[75] Inventors: Michael A. M. Boersma; Johannes M. Nanne; Martin F. M. Post, all of Amsterdam, Netherlands

[73] Assignee: Shell Oil Company, Houston, Tex.

[21] Appl. No.: 212,957

[22] Filed: Dec. 4, 1980

[30] Foreign Application Priority Data

Dec. 13, 1979 [NL] Netherlands .................. 7908984

[51] Int. Cl.³ .................... B01J 21/06; B01J 23/74
[52] U.S. Cl. ........................ 252/459; 252/431 N; 423/326
[58] Field of Search .............. 252/459, 431 N; 423/326–333

[56] References Cited

U.S. PATENT DOCUMENTS 4,208,305 6/1980 Kouwenhoven et al. ..... 252/431 N

*Primary Examiner*—Carl F. Dees
*Attorney, Agent, or Firm*—John M. Duncan; Ronald R. Reper

[57] ABSTRACT

An improved process for the preparation of certain crystalline iron silicates particularly suitable for converting acyclic oxygen-containing hydrocarbons into aromatic hydrocarbons wherein use of high silicon content compounds together with certain amines results in silicates having unexpected catalytic stability.

2 Claims, No Drawings

PROCESS FOR THE PREPARATION OF CRYSTALLINE SILICATES

BACKGROUND OF THE INVENTION

The invention relates to an improved process for the preparation of crystalline iron silicates.

Mixtures of carbon monoxide and hydrogen can be converted into aromatic hydrocarbon mixtures using a mixture of two catalysts of which one has the capability of catalyzing the conversion of an $H_2/CO$ mixture into acyclic oxygen-containing hydrocarbons and the other a crystalline iron or aluminum silicate having the capability of catalyzing the conversion of acyclic oxygen-containing hydrocarbons into aromatic hydrocarbons.

As described in U.S. Pat. No. 4,208,305 incorporated by reference, the crystalline silicates which are used in the catalyst mixtures may be prepared starting from an aqueous mixture containing the following compounds: one or more compounds of an alkali metal (M), one or more quaternary alkylammonium compounds ($R_4NX$), one or more silicon compounds and one or more iron or aluminum compounds.

The silicon compounds which are used in the preparation of the crystalline silicates may, on the basis of the $SiO_2$ content of the product that is obtained from these compounds after drying at 120° C. and calcining at 500° C., be divided into two classes, viz. silicon compounds yielding a product with an $SiO_2$ content of more than 90%w and silicon compounds yielding a product with an $SiO_2$ content of at most 90%w. For the sake of brevity, the silicon compounds which are suitable for use in the preparation of the crystalline silicates will, on the basis of the above-mentioned division, further be designated in this patent application as silicon compounds with a high and with a low $SiO_2$ content, respectively. Examples of silicon compounds with a high $SiO_2$ content are amophous solid silicas, silica sols, silica gels and silicic acid. An example of a silicon compound with a low $SiO_2$ content is water glass. The preparation of the crystalline silicates is performed by maintaining the mixture at elevated temperature until the crystalline silicate has been formed, separating it from the mother liquor and calcining it. In the aqueous mixture from which the silicates are prepared the various compounds should be present in the following ratio, expressed in moles of the oxides:

$M_2O$: $SiO_2 = 0.01-0.35$,
$(R_4N)_2O$: $SiO_2 = 0.01-0.4$,
$SiO_2$: $A_2O_3 > 10$, and
$H_2O$: $SiO_2 = 5-65$.

Although according to the above-mentioned procedure crystalline silicates with excellent catalytic properties can be prepared, the procedure has nevertheless a serious drawback, which is connected with the use of the quaternary alkylammonium compound and which drawback hampers use on a technical scale. Quaternary alkylammonium compounds are relatively costly compounds, which are virtually unsuitable for use in a catalyst preparation on a technical scale, in view of the quantities required in this procedure.

Applicant's have carried out an investigation concerning the preparation of the above-mentioned crystalline iron silicates, in which instead of quaternary alkylammonium compounds, amines with the general formula $R_1 R_2 R_3 N$ are used, in which $R_1$ represents an alkyl group and $R_2$ and $R_3$ represent an alkyl group or an hydrogen atom as shown, e.g., in silicate 22 of the aforesaid U.S. Pat. No. 4,208,305, employing a compound of low silicon content. In an investigation concerning the use of the above-mentioned catalyst mixtures, in which as the crystalline silicate there has been incorporated an iron silicate prepared using an alkylamine instead of a quaternary alkylammonium compound, for the preparation of aromatic hydrocarbon mixtures starting from $H_2/CO$ mixtures with an $H_2/CO$ molar ratio below 1.0, it has been found that the stability of these catalyst mixtures is determined to a large extent by the nature of the silicon compound present in the aqueous mixture from which the crystalline iron silicate component of the catalyst mixture is prepared. It has been found that catalyst mixtures with excellent stability for the conversion of $H_2/CO$ mixtures with an $H_2/CO$ molar ratio below 1.0 into aromatic hydrocarbon mixtures can be obtained by using in the catalyst mixtures a crystalline iron silicate component prepared from an aqueous mixture in which one or more amines with the general formula $R_1 R_2 R_3 N$ and one or more silicon compounds with a high $SiO_2$ content are present. The preparation of crystalline iron silicates having the properties mentioned hereinafter under (a)-(c), starting from an aqueous mixture in which one or more amines with the general formula $R_1 R_2 R_3 N$ and one or more silicon compounds with a high $SiO_2$ content are present, is novel.

SUMMARY OF THE INVENTION

The present invention application therefore relates to a novel procedure for the preparation of crystalline iron silicates having the following properties:

(a) thermally stable up to a temperature above 600° C., (b) an X-ray powder diffraction pattern showing, inter alia, the reflections given in Table A.

TABLE A

| Radiation : Cu - K $2\theta$ | Wavelength 0.15418nm relative intensity |
|---|---|
| 7.8–8.2 | S |
| 8.7–9.1 | M |
| 11.8–12.1 | W |
| 12.4–12.7 | W |
| 14.6–14.9 | W |
| 15.4–15.7 | W |
| 15.8–16.1 | W |
| 17.6–17.9 | W |
| 19.2–19.5 | W |
| 20.2–20.6 | W |
| 20.7–21.1 | W |
| 23.1–23.4 | VS |
| 23.8–24.1 | VS |
| 24.2–24.8 | S |
| 29.7–30.1 | M | wherein the letters used have the following meanings: VS = very strong; S = strong; M = moderate; W = weak; $\theta$ = angle according to Bragg.

(c) in the formula that represents the composition of the silicate, expressed in moles of the oxides, and in which, in addition to oxides of hydrogen, alkali metal and silicon iron oxide is present, the $SiO_2/Fe_2O_3$ molar ratio (m) is more than 10, which process comprises maintaining at a temperature below about 90° to about 300° C. for a period of 4 hours or more, until the crystalline silicate is formed, an aqueous mixture containing the following compounds: one or more compounds of an alkali metal (M), one or more amines with the general formula $R_1R_2R_3N$, in which $R_1$ represents an alkyl group and $R_2$ and $R_3$ represent an alkyl group or a hydrogen atom, one or more silicon compounds which yield, after drying at 120° C. and calcining at 500° C., a product with an $SiO_2$ content higher than 90%w of one or more iron compounds, in which mixture the compounds, with the exception of the amines, are present in the following molar ratios, expressed in moles of the oxides:

$M_2O$: $SiO_2 = 0.01-0.35$,
$R_1R_2R_3N$: $SiO_2 = 0.04-1.0$,
$SiO_2$: $Fe_2O_3 > 10$, and
$H_2O$: $SiO_2 = 5-65$, then separating said crystalline silicate from the mother liquor, and calcining said separated silicate.

DESCRIPTION OF PREFERRED EMBODIMENTS

The said crystalline iron silicates are characterized in that they have the following properties:

(a) thermally stable up to a temperature above 600° C., (b) an X-ray powder diffraction pattern showing, inter alia, the reflections given in Table A of the specification, and (c) in the formula that represents the composition of the silicate, expressed in moles of the oxides, and in which, in addition to oxides of hydrogen, alkali metal and silicon, there is present an oxide of a trivalent metal A selected from Al and Fe, the $SiO_2/A_2O_3$ molar ratio (for the sake of brevity further designated as m in this patent application) is more than 10.

Although the above-mentioned crystalline alluminum silicates are closely related to the crystalline iron silicates, as regards their preparation, structure and properties, the investigation by Applicant's have surprisingly shown that, while the nature of the silicon compound which is incorporated into the aqueous amine-containing mixture from which the crystalline iron silicate component of the catalyst mixture is prepared, has a great influence on the stability of the catalyst mixture for the conversion of $H_2/CO$ mixtures with an $H_2/CO$ molar ratio below 1.0 into aromatic hydrocarbon mixtures, the nature of the silicon compound incorporated into the aqueous amine-containing mixture from which the crystalline aluminum silicate component is prepared, does not affect the stability of the catalyst mixture for the above-mentioned use. When the crystalline aluminum silicates are employed, the catalyst mixtures are found to have a low stability for the above-mentioned use, irrespective of the nature of the silicon compound in the aqueous amine-containing mixture, from which they have been prepared.

In the investigation carried out by Applicant's it has further been found that the $M_2/SiO_2$ molar ratio of the aqueous mixture in which an amine and a silicon compound with high $SiO_2$ content are present and from which the crystalline iron silicate component of the catalyst mixture is prepared, has a great influence on the $C_3^+$ and $C_5^+$ selectivity of the catalyst mixture for the conversion of $H_2/CO$ mixtures into aromatic hydrocarbon mixtures. Said $M_2O/SiO_2$ molar ratio also influences the stability of the catalyst mixture. It has been found that catalyst mixtures with high $C_3^+$ and $C_5^+$ selectivity and excellent stability for the conversion of $H_2/CO$ mixtures into aromatic hydrocarbon mixtures can be obtained by using in the catalyst mixtures a crystalline iron silicate component prepared from the above-mentioned aqueous amine-containing mixtures in which one or more silicon compounds with a high $SiO_2$ content are present, provided that the $M_2O/SiO_2$ molar ratio in the aqueous mixture amounts to less than 0.12.

Although the crystalline silicates prepared according to the invention are designated as iron silicates, they may contain, in addition to iron, a small amount of aluminum. The silicon compounds which are suitable for the preparation of crystalline silicates on a technical scale, from an economic point of view contain as a rule a small amount of aluminum as contaminant. This aluminum is usually found, at least partly, in the silicate prepared.

The silicates prepared according to the invention have been defined, inter alia, with reference to the X-ray powder diffraction pattern. This pattern should contain, inter alia, the reflections shown in Table A. The complete X-ray powder diffraction pattern of a typical example of a silicate prepared according to the invention is shown in Table B (Radiation: Cu-K; wavelength: 0.15418 nm).

TABLE B

| $2\theta$ | relative intensity ($100 \cdot I/I_o$) | description |
|---|---|---|
| 8.00 | 55 | SP |
| 8.90 | 36 | SP |
| 9.10 | 20 | SR |
| 11.95 | 7 | NL |
| 12.55 | 3 | NL |
| 13.25 | 4 | NL |
| 13.95 | 10 | NL |
| 14.75 | 9 | BD |
| 15.55 | 7 | BD |
| 15.95 | 9 | BD |
| 17.75 | 5 | BD |
| 19.35 | 6 | NL |
| 20.40 | 9 | NL |
| 20.90 | 10 | NL |
| 21.80 | 4 | NL |
| 22.25 | 8 | NL |
| 23.25 | 100$^x$ | SP |
| 23.95 | 45 | SP |
| 24.40 | 27 | SP |
| 25.90 | 11 | BD |
| 26.70 | 9 | BD |
| 27.50 | 4 | NL |
| 29.30 | 7 | NL |
| 29.90 | 11 | BD |
| 31.25 | 2 | NL |
| 32.75 | 4 | NL |
| 34.40 | 4 | NL |
| 36.05 | 5 | BD |
| 37.50 | 4 | BD |
| 45.30 | 9 | BD |

$^xI_o$ = intensity of the strongest separate reflection present in the pattern.

The letters used in the Table B for describing the reflections have the following meanings: SP=sharp; SR=shoulder; NL=normal; BD=broad; $\theta$=angle according to Bragg.

According to the invention the crystalline iron silicates are prepared starting from an aqueous mixture containing the following compounds: one or more compounds of an alkali metal (M), one or more amines ($R_1 R_2 R_3 N$), one or more compounds with a high $SiO_2$ content and one or more iron compounds. The preparation of the silicates may be carried out either at atmospheric pressure or at elevated pressure. If reaction temperatures are used which lie above the boiling point of the mixture, it is preferred to work in an autoclave under autogenous pressure. The silicates are preferably prepared by maintaining the mixture, for at least four hours, at a temperature between 90° and 300° C., and particularly at a temperature between 125° and 175° C. After the silicates have been formed, the crystals are separated from the mother liquor, for instance by filtering, decanting or centrifuging. Thereupon, the crystal mass is washed with water and finally dried at a temperature between 100° and 200° C. and calcined, suitably at a temperature between 500°–1000° C. for a period of 0.1 hours or more.

As examples of suitable compounds for use in the preparation of the silicates according to the invention may be mentioned: nitrates, carbonates, hydroxides and oxides of alkali metals; linear and branched alkylamines; amorphous solid silicas, silica sols, silica gels and silicic acid; oxides, hydroxides, normal salts and complex salts of iron. In the preparation of the silicates according to the invention it is preferred to start from an aqueous mixture in which M is present in a sodium compound and $R_1 R_2 R_3 N$ is a linear primary alkylamine with 3–5 carbon atoms in the alkyl group, in particular n-butylamine. In the preparation of the silicates according to the invention it is further preferred to start from an aqueous mixture in which the silicon and iron compounds, expressed in moles of the oxides, are present in a ratio below 650 and particularly below 400.

Silicates prepared according to the invention may be used, inter alia, as adsorbent and extractant, as drying agent, as ion exchanger and as catalyst or catalyst carrier in different catalytic processes, in particular the catalytic preparation of aromatic hydrocarbons from acyclic organic compounds. If the aim is to use the silicates prepared according to the invention as catalyst or catalyst carrier, it is preferred previously to reduce the alkali metal content of these silicates to less than 0.1%w and in particular to less than 0.01%w. The reduction of the alkali metal content of the silicates can very suitably be carried out by contacting them once or several times with an aqueous solution containing ammonium ions. From the $NH_4^+$-silicates obtained in this way the $H^+$-silicates can be prepared by calcining. When the crystalline iron silicates are used as catalyst they may be combined, if desired, with a binder material such as bentonite or kaolin.

As explained hereinbefore, an important application of the silicates prepared according to the invention is their use in catalyst mixtures meant for the preparation of an aromatic hydrocarbon mixture from an $H_2/CO$ mixture. Such $H_2/CO$ mixtures can be prepared very conveniently by steam gasification of a carbon-containing material. Examples of such materials are brown coal, anthracite, coke, crude mineral oil and fractions thereof and oils recovered from tar sand and bituminous shale. The steam gasification is preferably carried out at a temperature between 900° and 1500° C. and a pressure between 10 and 50 bar. The preferred starting material for the preparation of an aromatic hydrocarbon mixture is an $H_2/CO$ mixture whose molar ratio lies between 0.25 and 1.0. The preparation of the aromatic hydrocarbon mixture, starting from an $H_2/CO$ mixture and using a catalyst mixture containing a crystalline iron silicate prepared according to the invention, is preferably carried out at a temperature of 200°–500° C., and in particular of 300°–450° C., a pressure of 1–50 bar, and in particular of 5–100 bar and a space velocity of 50–5000, and in particular of 300–3000 Nl gas/l catalyst/h. The two catalysts present in the catalyst mixture that is used in the preparation of an aromatic hydrocarbon mixture from an $H_2/CO$ mixture will for the sake of brevity, be further designated as catalysts X and Y. Catalyst X is the catalyst having the capability of catalyzing the conversion of an $H_2/CO$ mixture into acyclic oxygen-containing hydrocarbons and catalyst Y is the crystalline iron silicate prepared according to the invention. Preferred X-catalysts are those which are capable of converting an $H_2/CO$ mixture into substantially methanol and/or dimethyl ether. If the intention is to prepare a product substantially consisting of hydrocarbons boiling in the gasoline range, it is very suitable to use as the X-catalyst a catalyst containing zinc together with chromium. When such a catalyst is used, it is preferred to choose a catalyst in which the atomic zinc percentage, based on the sum of zinc and chromium, is at least 60% and in particular 60–80%. If the intention is to prepare, in addition to hydrocarbons boiling in the gasoline range, a fuel gas with high calorific value, it is very suitable to use as the X-catalyst a catalyst containing zinc together with copper. It is preferred to use a catalyst mixture containing per part by volume of catalyst Y 1–5 parts by volume of catalyst X.

The above-described conversion using a mixture of a crystalline iron silicate prepared according to the invention and a catalyst having the capability of catalyzing the conversion of an $H_2/CO$ mixture into acyclic oxygen-containing hydrocarbons, can also very suitably be used as the first step in a two-step process for the conversion of $H_2/CO$ mixtures into hydrocarbon mixtures. In this case, carbon monoxide and hydrogen present in the reaction product of the first step, optionally together with other components of this reaction product, are contacted in a second step with a catalyst containing one or more metal components having catalytic activity for the conversion of an $H_2/CO$ mixture into acyclic hydrocarbons, which metal components have been chosen from the group formed by cobalt, nickel and ruthenium, on the understanding that, if the feed for the second step has an $H_2/CO$ molar ratio of less than 1.5, water is added to this feed and that in the second step a bifunctional catalyst or catalyst combination is used which contains, in addition to the metal components having catalytic activity for the conversion of an $H_2/CO$ mixture into acyclic hydrocarbons, also one or more metal components having catalytic activity for the conversion of an $H_2O/CO$ mixture into an $H_2/CO_2$ mixture.

The above-described conversion using a mixture of a crystalline iron silicate prepared according to the invention and a catalyst having the capability of catalyzing the conversion of an $H_2/CO$ mixture into acyclic oxygen-containing hydrocarbons, can also very suitably be used as the first step in a three-step process for the preparation of a.o. middle distillates from an $H_2/CO$ mixture. In this case, carbon monoxide and hydrogen present in the reaction product of the first step, optionally together with other components of this reaction product, are contacted in a second step with a catalyst that contains 10–40 pbw cobalt and 0.25–5 pbw zirconium, titanium or chromium per 100 pbw silica and which has been prepared by impregnating a silica carrier with one or more aqueous solutions of salts of cobalt and zirconium, titanium or chromium followed by drying the composition, calcining it at 350°–700° C. and reducing it at 200°–350° C., on the understanding that, if the feed for the second step has an $H_2/CO$ molar ratio of less than 1.5, water is added to this feed and that the Co-impregnation catalyst is used in combination with a CO-shift catalyst. Of the reaction product of the second step, at least that part of which the initial boiling point lies above the final boiling point of the heaviest middle distillate desired as end product, is subjected to a catalytic hydrotreatment in a third step.

The invention will now be explained with reference to the following example.

EXAMPLE

Two crystalline silicates (silicates 1 and 2) were prepared by mixing a mixture of water glass and n-$C_4H_9NH_2$ in water with a mixture of $H_2SO_4$ and $Fe_2(SO_4)_3$ or $Al_2(SO_4)_3$ in water and heating the combined mixture at 150° C. in an autoclave under autogenous pressure for 24 hours.

Six crystalline silicates (silicates 3-8) were prepared by heating mixtures of NaOH, amorphous silica, $(C_3H_7)_4NOH$ or n-$C_4H_9NH_2$ and $NaAlO_2$ or $Fe(NO_3)_3$ in water at 150° C. in an autoclave under autogenous pressure and under stirring for 24 hours.

After the reaction mixtures had cooled down, the silicates formed were filtered off, washed with water until the pH of the wash water was about 8, dried at 120° C. and calcined at 500° C. The silicates 1-8 had the following properties:

(a) thermally stable up to a temperature above 800° C.,
(b) an X-ray powder diffraction pattern showing the reflections given in Table A,
(c) a value for m as given in Table C.

TABLE C

| Silicate No. | m | |
|---|---|---|
| | $SiO_2/Al_2O_3$ | $SiO_2/Fe_2O_3$ |
| 1 | 100 | — |
| 2 | — | 111 |
| 3 | — | 91 |
| 4 | 83 | — |
| 5 | — | 91 |
| 6 | — | 107 |
| 7 | — | 100 |
| 8 | — | 95 |

A mixture of amorphous silica, n-$C_4H_9NH_2$ and $Fe(NO_3)_3$ in water was prepared, which mixture had substantially the same composition as the one applied for the preparation of silicate 8, the only difference being that in the present case the mixture did not contain NaOH. An attempt to prepare a crystalline iron silicate from this sodium-free mixture by heating it at 150° C. in an autoclave under autogenous pressure and under stirring for 24 hours remained unsuccessful. The product was completely amorphous.

The amorphous silica used in the preparation of the silicates 3-8 yielded, after drying at 120° C. and calcining at 500° C., a product consisting of 99.97%w $SiO_2$. The water glass used in the preparation of the silicates 1 and 2 yielded, after drying at 120° C. and calcining at 500° C., a product consisting of 78%w $SiO_2$.

The molar composition of the aqueous mixtures from which the silicates 1-8 were prepared can be represented as follows:

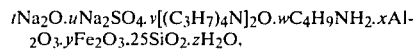

$tNa_2O.uNa_2SO_4.v[(C_3H_7)_4N]_2O.wC_4H_9NH_2.xAl_2O_3.yFe_2O_3.25SiO_2.zH_2O,$ in which t, u, v, w, x, y and z have the values mentioned in Table D.

TABLE D

| Silicate No. | t | u | v | w | x | y | z | $Na_2O/SiO_2$ molar ratio |
|---|---|---|---|---|---|---|---|---|
| 1 | 2 | 4.8 | — | 9.5 | 0.13 | — | 1045 | — |
| 2 | 2 | 5 2 | — | 9.8 | — | 0.27 | 518 | — |
| 3 | 3 | — | 4.5 | — | — | 0.20 | 450 | — |
| 4 | 4 | — | — | 10 7 | 0 22 | — | 468 | — |
| 5 | 4 | — | — | 10.0 | — | 0 20 | 450 | 0 16 |
| 6 | 2 5 | — | — | 10 0 | — | 0 25 | 0 450 | 0 10 |
| 7 | 2 5 | — | — | 10 0 | — | 0 25 | 450 | 0 10 |
| 8 | 1.0 | — | — | 10.0 | — | 0.25 | 450 | 0.04 |

The silicates 9-16 were prepared from the silicates 1-8, respectively, by boiling the silicates 1-8 with 1.0 molar $NH_4NO_3$ solution, washing with water, boiling again with 1.0 molar $NH_4NO_3$ solution and washing, drying at 120° C. and calcining at 500° C. Subsequently, eight catalyst mixtures (catalyst mixtures A-H) were prepared by mixing a $ZnO$-$Cr_2O_3$ composition, with rods of silicates 9-16. The atomic Zn percentage of the $ZnO$-$Cr_2O_3$ compositions, based on the sum of Zn and Cr, was 70%. The catalyst mixtures all contained per part by weight silicate 10 parts by weight of the $ZnO$-$Cr_2O_3$ composition.

The catalyst mixtures A-H were tested for the preparation of an aromatic hydrocarbon mixture from an $H_2/CO$ mixture. The test was carried out in a 50-ml reactor containing a fixed catalyst bed having a volume of 7.5 ml. In eight experiments an $H_2/CO$ mixture with an $H_2/CO$ molar ratio of 0.5 was conducted over each of the catalyst mixtures A-H at a temperature of 375° C., a pressure of 60 bar and a space velocity of 1000 $Nl.l^{-1}.h^{-1}$. In all cases a product was obtained of which the $C_5^+$ fraction consisted of more than 30%w aromatics. The other results of the experiments are listed in Table E.

TABLE E

| Experiment Number | Catalyst Number | Silicate Number | Conversion of the synthesis gas, % vol. | | Stability expressed as difference between $C_{10}$ and $C_{100}$ | $C_3^+$ selectivity averaged over 100 hours, %W | $C_5^+$ selectivity averaged over 100 hours, %W |
|---|---|---|---|---|---|---|---|
| | | | After 10 hours ($C_{10}$) | After 100 hours ($C_{100}$) | | | |
| 1 | A | 9 | 55 | 10 | 45 | — | — |
| 2 | B | 10 | 49 | 24 | 25 | — | — |
| 3 | C | 11 | 55 | 46 | 9 | — | — |
| 4 | D | 12 | 50 | 20 | 30 | — | — |
| 5 | E | 13 | 58 | 48 | 10 | 84 | 69 |
| 6 | F | 14 | 66 | 60 | 6 | 90 | 76 |
| 7 | G | 15 | 62 | 56 | 6 | 93 | 80 |
| 8 | H | 16 | 64 | 59 | 5 | 93 | 82 |

Of the silicates listed in Table D only the silicates 5-8 were prepared according to the invention. The silicates 1-4 are outside the scope of the invention. They have been included in the patent application for comparison. Of the experiments listed in Table E only the experiments 5-8 were carried out using a catalyst containing a crystalline iron silicate prepared according to the invention. The experiments 1-4 are outside the scope of the invention. They have been included in the patent application for comparison.

The results listed in Table E show that in the conversion of an $H_2/CO$ mixture into an aromatic hydrocarbon mixture, using a catalyst mixture whose crystalline aluminum silicate component has been prepared from an aqueous amine-containing base mixture, the stability of the catalyst mixture is independent of the nature of the silicon compound used in the preparation of the aluminum silicate. Both the use of a silicon compound with a high $SiO_2$ content and the use of a silicon compound with a low $SiO_2$ content lead to a catalyst mixture with a low stability for the said use. The results show further that when a catalyst mixture is used whose crystalline iron silicate component has been prepared from an aqueous amine-containing base mixture, the stability of the catalyst mixture for the said use greatly depends on the nature of the said silicon compound and that by a proper choice of this silicon compound, catalyst mixtures can be prepared with a good stability for the said conversion, which stability is comparable with that of a catalyst mixture whose crystalline iron silicate component has been prepared from an aqueous base mixture containing a tetrapropylammonium compound. The results show further that when a catalyst mixture is used whose crystalline iron silicate component has been prepared from an aqueous mixture in which an amine and a silicon compound with high $SiO_2$ content are present, the $C_3+$ and $C_5+$ selectivity of the catalyst mixture for the said use greatly depends on the $M_2O/SiO_2$ molar ratio in the aqueous mixture. This ratio also influences the stability of the catalyst mixture. By proper choice of this ratio, catalyst mixtures can be prepared with a high $C_3+$ and $C_5+$ selectivity and an excellent stability for the said conversion.

What is claimed is:

1. Crystalline iron silicates having the following properties:

(a) thermally stable up to a temperature above 600° C.,
(b) an X-ray powder diffraction pattern showing, inter alia, the reflections given in Table A of the specification,
(c) in the formula that represents the composition of the silicate, expressed in moles of the oxides, and in which, in addition to oxides of hydrogen, alkali metal and silicon iron oxide is present, the $SiO_2/Fe_2O_3$ molar ratio (m) is more than 10, which process comprises said silicates being prepared according to a process which comprises maintaining at a temperature between about 90° to about 300° C. for a period of 4 hours or more, until the crystalline silicate is formed, an aqueous mixture containing the following compounds:

one or more compounds of an alkali metal (M), one or more amines with the general formula $R_1R_2R_3N$, in which $R_1$ represents an alkyl group and $R_2$ and $R_3$ represent an alkyl group or a hydrogen atom, one or more silicon compounds which yield, after drying at 120° C. and calcining at 500° C., a product with an $SiO_2$ content higher than 90%w and one or more iron compounds, in which mixture the compounds, with the exception of the amines, are present in the following molar ratios, expressed in moles of the oxides:

$M_2O: SiO_2 = 0.01-0.35$,
$R_1R_2R_3N: SiO_2 = 0.04-1.0$,
$SiO_2: Fe_2O_3 > 10$, and
$H_2O: SiO_2 = 5-65$, then separating said crystalline silicate from the mother liquor, and calcining said separated silicate.

2. Crystalline silicates according to claim 1 wherein in the aqueous mixture the alkali metal compound is a sodium compound; the $R_1R_2R_3N$ compound is a linear primary alkylamine with 3–5 carbon atoms in the alkyl group; the molar ratio of the silicon and iron compounds expressed in moles of oxides is below 400; and the $M_2O/SiO_2$ molar ratio is 0.12 or lower.

* * * * *